(12) United States Patent
Feriani et al.

(10) Patent No.: US 9,089,662 B2
(45) Date of Patent: Jul. 28, 2015

(54) SELF-SENSING DISPENSING DEVICE FOR A CLEANING SOLUTION OR FABRIC SOFTENER

(71) Applicant: Henkel AG & Co. KGaA, Duesseldorf (DE)

(72) Inventors: Amir Feriani, Auvernier (CH); Cedric Zaugg, Neuchatel (CH); Jean-Paul Sandoz, Cormondreche (CH); Joseph Hess, Bevaix (CH)

(73) Assignee: Henkel AG & Co. KGaA, Duesseldorf (DE)

( * ) Notice: Subject to any disclaimer, the term of this patent is extended or adjusted under 35 U.S.C. 154(b) by 103 days.

(21) Appl. No.: 13/892,372

(22) Filed: May 13, 2013

(65) Prior Publication Data

US 2013/0248559 A1 Sep. 26, 2013

Related U.S. Application Data

(62) Division of application No. 12/705,450, filed on Feb. 12, 2010, now abandoned.

(30) Foreign Application Priority Data

Feb. 10, 2009 (EP) .................................. 09152483

(51) Int. Cl.
*B05B 12/12* (2006.01)
*A61M 15/00* (2006.01)
(Continued)

(52) U.S. Cl.
CPC .......... *A61M 15/0091* (2013.01); *A47K 5/1217* (2013.01); *A61L 2/22* (2013.01);
(Continued)

(58) Field of Classification Search
USPC .......................... 222/52, 504, 180–181.3, 196
See application file for complete search history.

(56) References Cited

U.S. PATENT DOCUMENTS 3,273,752 A   9/1966  Horeczky
3,917,172 A * 11/1975  O'Hare .......................... 239/305
(Continued)

FOREIGN PATENT DOCUMENTS

EP   0923957 A1   6/1999
EP   1129741 A2   9/2001
(Continued)

OTHER PUBLICATIONS

European Search Report (EP 09152483) dated Mar. 8, 2009.

*Primary Examiner* — Donnell Long
(74) *Attorney, Agent, or Firm* — P. Scott Smith

(57) ABSTRACT

The present liquid dispenser comprising a self-sensing dispensing device, fabric softener comprising a power supply means; a liquid dispensing element comprising an actuator and a dispensing; electronic control means operable to control said actuator; liquid supply means; valving means for allowing or blocking liquid to flow from said reservoir through said liquid supply means to said liquid dispensing element, wherein said actuator is operable to execute in itself at least a dispensing function and a detecting function, the detecting function detecting at least characteristics external to the self-sensing dispensing device and causing said actuator to generate a command signal, and wherein said electronic control means is operable to control said valving means and said actuator based on the reception of said command signal; wherein said electronic control means and said piezoelectric actuator are arranged to detect presence or movement of an object in the proximity of said piezoelectric actuator.

9 Claims, 3 Drawing Sheets

(51) Int. Cl.
- *A47K 5/12* (2006.01)
- *A61L 2/22* (2006.01)
- *A61L 9/14* (2006.01)
- *A61M 11/00* (2006.01)
- *B05B 17/06* (2006.01)
- *A61M 16/00* (2006.01)
- *B05B 1/30* (2006.01)
- *B05B 17/00* (2006.01)

(52) U.S. Cl.
CPC ............ *A61L 9/14* (2013.01); *A61M 11/00* (2013.01); *A61M 15/0085* (2013.01); *B05B 12/12* (2013.01); *B05B 12/122* (2013.01); *B05B 17/0607* (2013.01); *B05B 17/0684* (2013.01); *A61L 2202/14* (2013.01); *A61L 2209/11* (2013.01); *A61L 2209/111* (2013.01); *A61L 2209/132* (2013.01); *A61M 2016/0018* (2013.01); *A61M 2016/0021* (2013.01); *A61M 2016/0039* (2013.01); *A61M 2205/14* (2013.01); *A61M 2205/8206* (2013.01); *B05B 1/3053* (2013.01); *B05B 17/0646* (2013.01)

(56) References Cited

U.S. PATENT DOCUMENTS

| | | | | |
|---|---|---|---|---|
| 3,960,324 | A * | 6/1976 | Titus et al. | 239/4 |
| 3,974,941 | A * | 8/1976 | Mettler | 222/646 |
| 4,218,013 | A * | 8/1980 | Davison | 239/74 |
| 4,659,014 | A * | 4/1987 | Soth et al. | 239/102.2 |
| 4,839,039 | A * | 6/1989 | Parsons et al. | 210/143 |
| 5,301,873 | A * | 4/1994 | Burke et al. | 237/53 |
| 6,405,934 | B1 | 6/2002 | Hess et al. | |
| 6,820,821 | B2 | 11/2004 | Linstedt et al. | |
| 6,978,941 | B2 * | 12/2005 | Litherland et al. | 239/4 |
| 6,991,184 | B2 * | 1/2006 | Romaine | 239/318 |
| 7,155,758 | B1 * | 1/2007 | Berke et al. | 4/675 |
| 2003/0146300 | A1 | 8/2003 | Denyer et al. | |
| 2004/0004133 | A1 | 1/2004 | Ivri et al. | |
| 2007/0216256 | A1 | 9/2007 | Vogeley | |
| 2008/0110453 | A1 | 5/2008 | Ross et al. | |

FOREIGN PATENT DOCUMENTS

| | | |
|---|---|---|
| EP | 1681001 A2 | 7/2006 |
| EP | 1043162 B1 | 3/2007 |
| WO | 2006/059059 A1 | 6/2006 |

\* cited by examiner

Data Acquisition and Processing:

Data Acquisition and Processing:

SELF-SENSING DISPENSING DEVICE FOR A CLEANING SOLUTION OR FABRIC SOFTENER

FIELD OF THE INVENTION

The present invention generally relates to a self-sensing dispensing device, suitable for dispensing liquid substances, such as by activating a flow or a spray of droplets. Such device normally contains a dispensing body on a support part, in particular, a spout or a nozzle body of a liquid droplet spray device which dispenses a liquid substance from the device through the dispensing body. Such activation may be carried out by valving means to allow a flow and/or by pumping or pressurizing means. Such activation may further be carried out by a piezoelectric actuator used as a vibrating element for causing the liquid to vibrate so to be accelerated and expelled. A typical device further may consist of elements such as a liquid space, liquid feed and fluid interface to a reservoir, a reservoir as well as electrical connections between the vibrating element and a corresponding electronic circuitry. The liquid may be for example an ambient fragrance, a perfume, an insecticide, a fungicide, a fabric softener, an aromatherapy essence, a cleaning solution, a liquid pharmaceutical formulation, a lotion, cream, emulsion, aqueous based liquids and flammable or combustible liquids.

BACKGROUND OF THE INVENTION

Such dispensing bodies are sometimes called spouts, aperture plates, nozzle arrays, dosing apertures, orifice plates, vibratable membranes, atomizer, vibrating plate, dosing aperture arrangements, aerosol generators and the like. Such terms are hence to be understood as being interchangeable throughout the present document.

In fact such dispensing bodies and liquid dispensing devices are well known. For example see the document EP 1 129 741 in the name of the present Applicant. This document describes a dispensing device for spraying liquid and has a top substrate formed of a main body and of a nozzle body. The nozzle body contains a nozzle array of liquid droplet outlet means allowing a liquid substance contained in the liquid droplet spray device to exit the device, in this case as a spray of droplets. A piezoelectric actuator is used to cause the liquid to undergo a vibration so as to generate the droplet spray.

Generally, such piezoelectric actuator is driven so as to oscillate at or near an appropriate frequency to improve energy efficiency.

The document EP 1 043 162 describes an inkjet apparatus having a liquid detection method using an infrared detector to determine if liquid has passed through a spray path or not. Control means are provided to adjust the spraying itself.

The document US 2007/0216256 describes a drive control circuit for a piezoelectric activated pump. By measuring the internal impedance of the piezoelectric actuator, it is possible to control the operation frequency.

Document US2003/0146300 describes a nebulizer for nebulizing a substance and a reservoir having a metering chamber arranged so as to feed a substance to be nebulized from the nebulization device and a second chamber arranged to hold and retain any of this substance in excess of the volume held in the metering chamber. The device allows detecting the ejection of a unit dose.

However, a simplified and reliable controlled activation and deactivation of the actuator would be useful if the actuator could function by itself so as also to detect dispensing conditions and to control and/or monitor liquid dispense actuation.

It is, therefore, an object of the present invention to provide an innovative dispensing device that overcomes the inconveniences and limitations presented by the prior art documents.

Thus, the present invention concerns a dispensing device fulfilling these objectives efficiently which may be obtained in a relatively simple and inexpensive manner, as defined in the appended claims. The device is further capable of indirectly triggering and monitoring itself.

Furthermore, other desirable features and characteristics of the present invention will become apparent from the subsequent detailed description of the invention and the appended claims, taken in conjunction with the accompanying drawings and this background of the invention.

BRIEF SUMMARY OF THE INVENTION

Liquid dispenser comprising: a self-sensing dispensing device for a cleaning solution, fabric softener comprising: power supply means; a liquid dispensing element comprising an actuator and a dispensing aperture through which liquid is to be dispensed by activation of the actuator; electronic control means operable to control said actuator; liquid supply means for connecting with a liquid reservoir to supply liquid from said reservoir to said liquid dispensing element; valving means for allowing or blocking liquid to flow from said reservoir through said liquid supply means to said liquid dispensing element; wherein said actuator is operable to execute in itself at least a dispensing function and a detecting function, the detecting function detecting at least characteristics external to the self-sensing dispensing device and causing said actuator to generate a command signal; and wherein said electronic control means is operable to control said valving means and said actuator based on the reception of said command signal, wherein said electronic control means and said piezoelectric actuator being arranged to detect presence or movement of an object in the proximity of said piezoelectric actuator.

BRIEF DESCRIPTION OF THE DRAWINGS

The present invention will hereinafter be described in conjunction with the following drawing figures, wherein like numerals denote like elements.

DETAILED DESCRIPTION OF THE INVENTION

The following detailed description of the invention is merely exemplary in nature and is not intended to limit the invention or the application and uses of the invention. Furthermore, there is no intention to be bound by any theory presented in the preceding background of the invention or the following detailed description of the invention.

Thanks to the features of the self-sensing dispensing device according to the present invention, it is possible to reliably control the operation of the liquid dispensing device, and this without requiring any separate sensor.

Other features and advantages of the self-sensing dispensing device according to the present invention will become clear from reading the following description, which is given solely by way of a non-limitative example thereby referring to the attached drawings.

An example of preferred embodiments will now be described while referring to the figures. Generally, the self-sensing dispensing device according to the present invention is used to control the operation of an actuator in a liquid dispensing device.

Figure 1A:
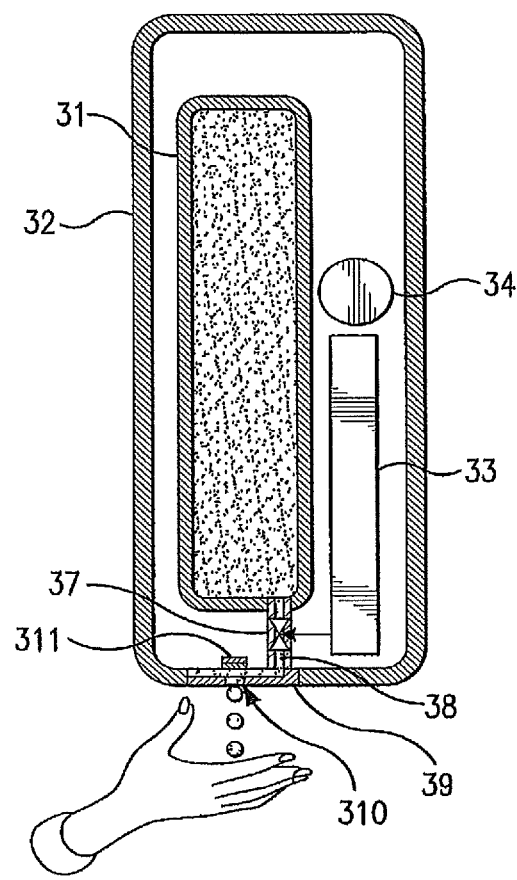
FIG. 1a shows a first example of a self-sensing piezoelectric dispensing device in a embodiment according to the present invention used in a liquid dispenser with a hand proximity detection.
Figure 1B:
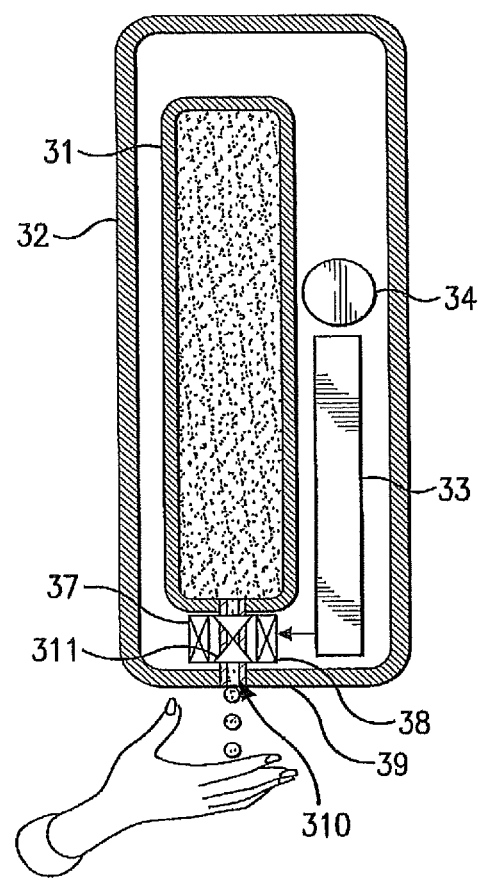
FIG. 1b shows a second example of a self-sensing electromagnetic dispensing device in the embodiment.
Figure 1C:
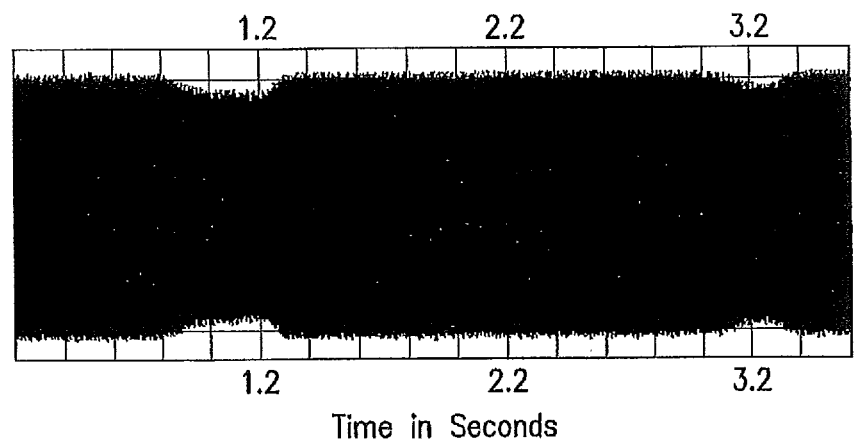
FIGS. 1c and 1d show examples of signals used in the hand proximity detection in the embodiment.
Figure 1D:
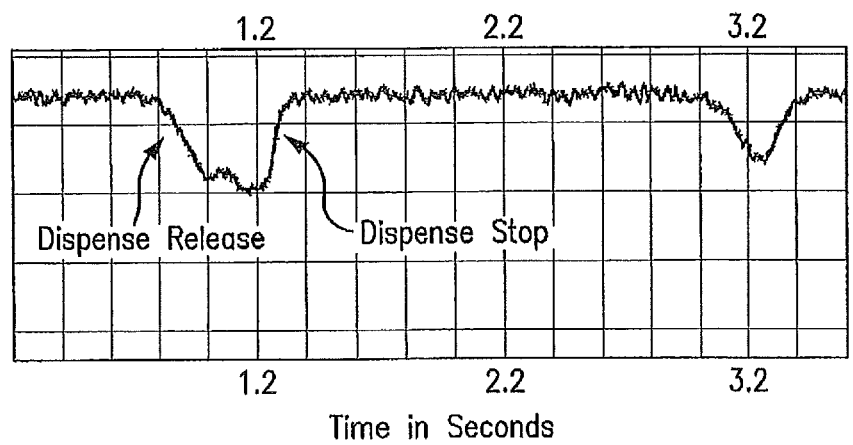

FIG. 1a shows a first example of a self-sensing piezoelectric dispensing device in the embodiment according to the present invention used in a liquid dispenser.

In this embodiment, the piezoelectric actuator 311 is also used as a proximity sensor, for example for detecting the presence of a hand passing in front of the dispenser, thus allowing to control release of the substance to be dispensed. As an example, the liquid dispenser may release soap from a spout onto a hand.

A housing 32 is provided comprising a reservoir 31 for containing liquid to be dispensed. Also provided are a battery 34 and electronic control means 33 for controlling the release of liquid, by way of signals sent by the piezoelectric actuator.

Thus, here too, any release of liquid from reservoir 31, and thus from the dispensing device is controlled by signals provided by the piezoelectric actuator 311.

Indeed, as can be seen from FIG. 3a, again inlet means are provided for providing a fluidic connection between reservoir 31 and a dispensing element, here dispensing head 39 by way of valving means such as an electro-valve 37. Dispensing head 39 comprises a dispensing aperture 310, for example a spout, having one or more nozzles through which the liquid is to be dispensed. A piezoelectric actuator 311 is also provided in the dispensing head to allow control of electro-valve 37, by detection of the proximity of a hand, and thus of the release of liquid from the reservoir, and ultimately from the dispensing device.

FIG. 3b shows a second example of a self-sensing dispensing device in the embodiment. It merely differs from the above first example in that the self-sensing dispensing device comprises an electromagnetic dispenser instead of a piezoelectric dispenser. The other parts are identical to those of FIG. 3a and are identified by the same reference numerals. Thus, an electromagnetic actuator 47 is used instead of a piezoelectric actuator. The windings of this electromagnetic actuator may be used for example to detect perturbations in an electromagnetic field caused by the presence or movement of a hand in its proximity.

In this embodiment, and indeed in all other embodiments too, the dispenser may be arranged to emit an appropriate electrical signal to detect reflection thereof, by way of analysis of the return signal. As such, any movement, object or presence below the actuator can be detected. Such analysis of a return signal is well known as such to a person skilled in the art. Thus, in the first example of the embodiment where the self-sensing dispensing device may be, for example, a soap dispenser, when a hand arrives in the proximity of the dispenser, its presence is detected by the return signal bouncing off the hand. This return signal is then analyzed by the electronic control means 33 in order to control the valving means, so as to allow liquid to flow from reservoir 31 to dispensing head 39, and ultimately to leave the dispensing device onto the hand below it. Once the hand is removed, the return signal will change so that this can also be detected therefore allowing to stop the dispensing operation by closing the valving means.

FIGS. 3c and 3d shows examples of signals used in a hand proximity detection in the second example of the embodiment.

As can be seen, the proximity and the absence of proximity can be readily detected by appropriate time-frequency analysis of the signals shown in FIG. 3c and FIG. 3d.

As can be understood from the description of the above embodiments, a smart dispensing device may be obtained by using a self-sensing dispenser.

Actuation can be triggered by presence detection or by motion detection.

Additional advantages of the self-sensing dispensing device according to the present invention concern the fact that sensing and dispensing actions are carried out by the same component. In conventional devices, a dispensing device could continue to dispense even when the separate sensor has failed, thus leading to waste of the dispensed liquid. For an inhaler, this could even be dangerous to a patient, as the inhaled dose may be much higher than permitted.

Clearly, a cheaper device may also be obtained, as no separate sensor needs to be provided, connected and calibrated.

Further, the dispensing device according to the present invention may be provided with self-learning technology. For example, the electronic control means may be provided with a memory for storing detection results and to allow for a self-calibration, by comparing with previously stored detection results. For instance, the electronic control means may analyze the envelope of the command signal generated by the actuator by comparing it with pre-stored signals, the result of this comparison allowing to trigger the actuation means.

Moreover, the present self-sensing piezoelectric dispenser may even detect clogging, as this leads to modification of the electro-mechanical characteristic of the self-sensing piezoelectric dispenser.

Also, an empty detection in the dispenser can be performed in this manner, so the piezoelectric actuator can be stopped.

Having described now the preferred embodiments of this invention, it will be apparent to one of skill in the art that other embodiments incorporating its concept may be used. It is felt, therefore, that this invention should not be limited to the disclosed embodiments, but rather should be limited only by the scope of the appended claims.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. Liquid dispenser comprising:
   a self-sensing dispensing device for a cleaning solution, fabric softener comprising:
   power supply means,
   a liquid dispensing element comprising an actuator and a dispensing aperture through which liquid is to be dispensed by activation of the actuator,
   electronic control means operable to control said actuator, liquid supply means for connecting with a liquid reservoir to supply liquid from said reservoir to said liquid dispensing element, valving means for allowing or blocking liquid to flow from said reservoir through said liquid supply means to said liquid dispensing element, wherein said actuator is operable to execute in itself at least a dispensing function and a detecting function, the detecting function detecting at least characteristics external to the self-sensing dispensing device and causing said actuator to generate a command signal, and wherein said electronic control means is operable to control said valving means and said actuator based on the reception of said command signal, wherein said electronic control means and said actuator being arranged to detect presence or movement of an object in the proximity of said piezoelectric actuator.

2. The self-sensing dispensing device of claim 1, wherein said electronic control means is operable to open and/or close said valving means based on said command signal.

3. The self-sensing dispensing device of claim 2, wherein said electronic control means is operable to turn on and off said self-sensing dispensing device based on said command signal.

4. The self-sensing dispensing of claim 1, wherein said electronic control means is operable to analyze a time-frequency response of said command signal, the result of said analysis allowing to trigger said valving means.

5. The self-sensing dispensing of claim 4, wherein said electronic control means comprises memory means for storing results of said analysis for self-learning purposes.

6. The self-sensing dispensing device of claim 1, wherein said actuator is a piezoelectric actuator.

7. Household appliance comprising the self-sensing dispensing device of claim 6.

8. The self-sensing dispensing device of claim 1, wherein said actuator is an electromagnetic actuator.

9. Liquid dispenser comprising:

the self-sensing dispensing device of claim 8, said dispensing element having at least one outlet for dispensing said liquid as a flow, and said electronic control means and said electromagnetic actuator being arranged to detect presence or movement of an object in the proximity of said electromagnetic actuator.

* * * * *